( 12 ) United States Patent
Huhn et al.

(10) Patent No.: US 9,004,280 B2
(45) Date of Patent: Apr. 14, 2015

(54) SINGLE-DOSE PACKAGE FOR TRANSDERMAL THERAPEUTIC SYSTEM OR SHEET-LIKE ADMINISTRATION FORMS

(71) Applicants: Ralf Huhn, Koenigswinter (DE); Petra Botzem, Andernach (DE); Arno Schmidt, Marienrachdorf (DE); Tobias Schueller, Mendig (DE)

(72) Inventors: Ralf Huhn, Koenigswinter (DE); Petra Botzem, Andernach (DE); Arno Schmidt, Marienrachdorf (DE); Tobias Schueller, Mendig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 14/155,532

(22) Filed: Jan. 15, 2014

(65) Prior Publication Data

US 2014/0190855 A1    Jul. 10, 2014

Related U.S. Application Data

(63) Continuation-in-part of application No. PCT/EP2012/002983, filed on Jul. 16, 2012.

(51) Int. Cl.
*B65D 73/00*   (2006.01)
*A61B 19/02*   (2006.01)
*B65D 75/30*   (2006.01)
*B65D 75/58*   (2006.01)
*B32B 15/20*   (2006.01)

(52) U.S. Cl.
CPC .............. *A61B 19/026* (2013.01); *B65D 75/30* (2013.01); *B65D 75/5805* (2013.01); *B32B 15/20* (2013.01); *B32B 2307/31* (2013.01); *B32B 2439/46* (2013.01)

(58) Field of Classification Search
CPC .... B65D 75/68; B65D 75/5833; B65D 75/66; B65D 75/5838; B65D 75/5827
USPC ............ 229/87.05; 206/438, 439, 484, 484.1, 206/484.2, 532; 383/105, 116, 200
See application file for complete search history.

(56) References Cited

U.S. PATENT DOCUMENTS

| | | | | |
|---|---|---|---|---|
| 2,552,340 | A * | 5/1951 | Moore | 229/87.05 |
| 2,835,435 | A * | 5/1958 | Mullinix | 229/87.05 |
| 4,801,006 | A * | 1/1989 | Martin et al. | 119/170 |
| 4,834,241 | A * | 5/1989 | Southern | 206/459.5 |
| 5,439,133 | A * | 8/1995 | Stone | 229/122.32 |
| 5,515,965 | A * | 5/1996 | Boldrini et al. | 206/264 |
| 6,318,625 | B1 * | 11/2001 | Muller et al. | 229/87.05 |

(Continued)

FOREIGN PATENT DOCUMENTS

| | | |
|---|---|---|
| DE | 20 2004 003 781 U1 | 6/2004 |
| DE | 10 2006 041 921 A1 | 3/2008 |
| DE | 10 2009 008 271 A1 | 8/2010 |

*Primary Examiner* — Jacob K Ackun
(74) *Attorney, Agent, or Firm* — R. S. Lombard; K. Bach

(57) ABSTRACT

In the case of a package (1) for single-dose films (2) containing active substances, comprising an upper packaging material element (3) and a lower packaging material element (4) which are connected together by a peripheral seal area or respectively sealing seam (5) such that a cavity (6) for holding the film (2) is formed, said cavity being enclosed on all sides, wherein
the upper packaging material element (3) and the lower packaging material element (4) each have at least one cut (7, 8) in the region of the seal area or respectively, the sealing seam (5), said cuts being congruent, and
at least one cut (7, 8) is crossed by a folding or bending line (10),
the folding or bending line (10) is formed in a weakened manner.

4 Claims, 2 Drawing Sheets

(56) References Cited

U.S. PATENT DOCUMENTS

| | | |
|---|---|---|
| 6,702,178 B2 * | 3/2004 | Bowers et al. ............ 229/87.08 |
| 2004/0031843 A1 * | 2/2004 | Ronan ........................ 229/153 |
| 2006/0023976 A1 | 2/2006 | Alvater et al. |
| 2006/0131204 A1 | 6/2006 | Geser et al. |
| 2008/0105582 A1 | 5/2008 | Ludwig et al. |
| 2009/0283440 A1 | 11/2009 | Krumme |

* cited by examiner

SINGLE-DOSE PACKAGE FOR TRANSDERMAL THERAPEUTIC SYSTEM OR SHEET-LIKE ADMINISTRATION FORMS

CROSS-REFERENCE TO RELATED APPLICATION

This is a continuation-in-part application of pending international application PCT/EP2012/002983 filed Jul. 16, 2012 and claiming the priority of German Application No. 10 2011 107 939.8 filed Jul. 19, 2011 which is hereby incorporated by reference in its entirety.

BACKGROUND OF THE INVENTION

The invention relates to a package for single-dose films containing active substances, comprising an upper packaging material element and a lower packaging material element which are connected together by a peripheral sealing surface or sealing seam such that a cavity for holding the film is formed, said cavity being enclosed on all sides, wherein the upper packaging material element and the lower packaging material element each have at least one cut in the region of the sealing surface or sealing seam, said cuts being congruent, and at least one cut is crossed by a folding or bending line.

A package of the abovementioned type is known from the German laid-open patent application DE 10 2009 008 217 A1.

DE 10 2004 047 445 A1 discloses a non-reclosable package for products that are harmful to health, in particular pharmaceutical products, comprising a first packaging material element and a second packaging material element. In this case, the two packaging material elements are arranged in a superposed manner and the package has at least one first surface portion, at the edge or edges of which the two packaging material elements are connected together in a releasable manner, wherein at least one cavity for holding the packaging material is formed between the two packaging material elements, said cavity being enclosed on all sides. The package has at least one second surface portion which is located outside said first surface portion or adjoins the latter and at the edge or edges of which the two packaging material elements are connected together in a releasable manner and wherein at least one of the two packaging material elements is provided with at least one structure which extends within the second surface portion and which allows the packaging material element/elements to be torn into.

DE 10 2006 041 921 A1 discloses a package for films containing an active substance, which has a carrier layer and a top layer releasably connected thereto. The package has in this case a paired arrangement of two opposite surface regions which are separated from one another by a web and within which the top layer is not connected to the carrier layer, with the result that two spaces for receiving said films in pairs are formed, said spaces being separated from one another and enclosed on all sides. Provided within said web is a further surface region in which the carrier layer is not connected to the top layer, with the result that a cavity that is enclosed on all sides is formed and at least one perforation line is provided within the web.

In the known designs of the package, the user has to bend over a part of the package along a printed-on marking line in order subsequently to open the package at a likewise marked location by tearing along a weakening line. Bending over along the printed-on marking line changes the position of a structure or of a cut in the region of the sealing surface or sealing seam of the two packaging material elements to the edge of the package and thus makes it possible to tear open the package in order to be able to remove the contents from the cavity. The structure or the cut has a length of approximately 3 to 5 mm. The printed-on marking line crosses the structure or the cut preferably at right angles or at a selected angle. Depending on the structure and material selection of the packaging material elements, when bending over takes place, the length of the structure or of the cut is not folded centrally but rather such that two legs of the structure or of the cut that have different lengths are formed. In the worst case, the structure or the cut is not moved to the edge at all. As a result, tearing-in of the package is rendered difficult or even prevented, since the structure/cut intended to be a tearing-in aid does not come into use.

Therefore, the invention is based on the object of creating a single-dose package of the generic type, which improves the above-described designs, and in particular simplifies the handling thereof.

SUMMARY OF THE INVENTION

This object is achieved according to the invention in that the folding or bending line is formed in a weakened manner.

Refinements of the invention are given in the dependent claims.

The invention thus provides for the outer layer of the upper packaging material element to be weakened along the folding or bending line in order to allow bending over to take place at precisely this position. As a result of the weakening, the structure or the cut is flapped over precisely in the centre and the tearing-in location is always positioned at the edge of the package.

The weakening is carried out in particular such that only the outer layer of the packaging material element is altered or processed. The subsequent metal foil is not stressed at all or only a little. The weakening can be produced for example by perforation, notch punching, scoring or by laser ablation. However, other processing forms are expressly desired.

The outer layer is preferably imprintable so that for example product identifications and tearing-open suggestions can be applied. The weakening can in this case take up the entire thickness of the outer layer or only a partial height. Whereas in the case of scoring the outer layer is displaced, in the case for example of laser ablation, the material can be removed down to the subsequent metal layer.

A second layer or, in the case of a three-layered structure, the middle layer consists of a metal foil, preferably aluminium, having a thickness of 9-25 micrometers. This metal layer ensures the tightness of the package with respect to moisture and air.

The inner layer is a sealable plastics layer, wherein the sealing seam produced by this layer cannot be opened again.

In a preferred embodiment, the upper packaging material element and the lower packaging material element have an identical structure. This has the advantage that only one sort of packaging material is used and thus a mix-up is precluded.

The connection between the two packaging material elements is preferably produced by sealing or welding. Suitable means and methods for producing the sealing surfaces or the sealing seams are known to a person skilled in the art. The seal serves as a diffusion and permeation barrier and is generally impermeable for active substances and humidity. Both hot sealing methods and cold sealing methods may be used. It is possible to use for example hot-melt adhesives, sealing waxes, sealing dispersions or adhesives.

In a further embodiment, two cuts that are oriented in parallel are introduced into the sealing surface or the sealing seam. These cuts are arranged such that the continuation of the cuts, that is to say of the tearing lines, extend through the cavity. If both sealing edges are torn off, the film containing active substance can be pushed out of the cavity. In this case, the folding or bending line is arranged in a preferred configuration such that the two cuts cross at right angles. In the event of bending over taking place along the weakened folding or bending line, both cuts are then moved to the edge and thus two tearing-in locations are created.

BRIEF DESCRIPTION OF THE DRAWINGS

Further features and details of the invention can be gathered from the claims and the following description of exemplary embodiments of the invention that are illustrated in schematic drawings, in which:

DETAILED DESCRIPTION OF THE INVENTION

Figure 1:
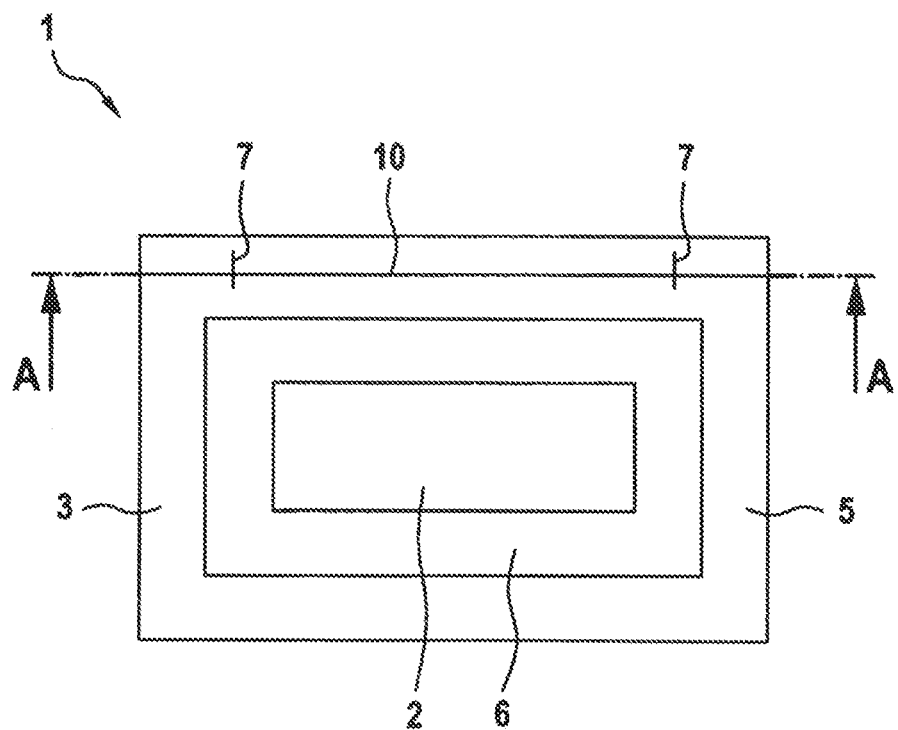
FIG. 1 shows a plan view of a package for films containing active substance.

FIG. 1 illustrates a plan view of the package 1 according to the invention. The package 1 is a sealed-edge bag composed of an upper packaging material element 3 and a lower packaging material element 4. Between the upper packaging material element 3 and the lower packaging material element 4, a film 2 containing an active substance is arranged in a cavity 6 that is enclosed on all sides. The cavity 6 is produced by a peripheral seal area or respectively sealing seam 5 which connects the two packaging material elements 3, 4 in a non-releasable manner. Within the seal area or respectively sealing seam 5, a cut 7 is located in the upper packaging material element 3 and a cut 8 is located in the lower packaging material element 4. The two cuts 7 and 8 are congruent. The cut 7 is crossed by a folding or bending line 10.

Figure 2:
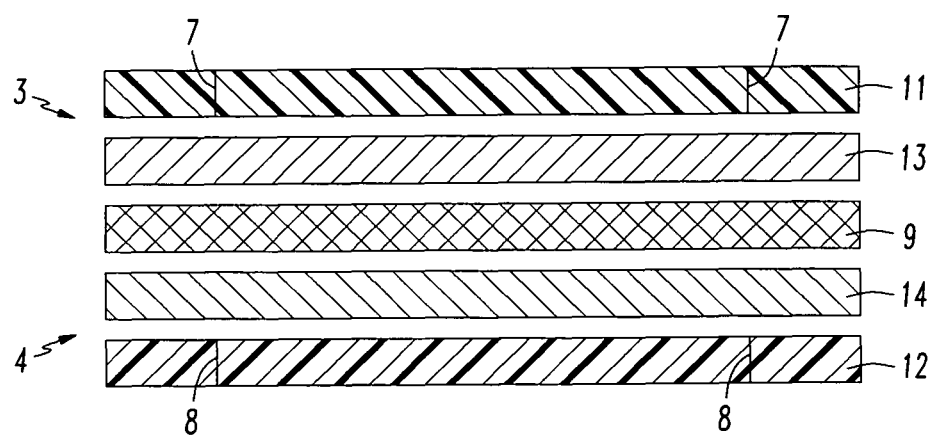
FIG. 2 shows a sectional side view of the package from FIG. 1.

FIG. 2 illustrates the structure of the package in a sectional illustration along the line A-A in FIG. 1. The individual parts are shown on a much larger scale and in a separated manner in order to clarify the structure. The upper packaging material element 3 consists at least of an upper, outer layer 11 and a subsequent upper metal layer 13.

The lower packaging material layer 4 likewise consists of a lower, outer layer 12 and a subsequent lower metal layer 14.

The metal layers 13, 14 consist preferably of an aluminium foil having a thickness of 9 to 25 micrometers. This foil ensures that the inserted product does not come into contact with air and is exposed to no moisture whatsoever.

The upper or the lower packaging material element 3, 4 has a sealable layer 9 at least in the region of the seal area or respectively of the sealing seam 5. However, the sealable layer 9 may also be applied to both, upper and lower, packaging is material elements 3, 4. The seal area or respectively sealing seam 5 produced by this layer 9 cannot be separated again.

LIST OF REFERENCE SIGNS

1 Package
2 Film containing active substance
3 Upper packaging material element
4 Lower packaging material element
5 Seal area or respectively sealing seam
6 Cavity
7 Cut
8 Cut
9 Sealing layer
10 Folding or bending line
11 Upper, outer layer
12 Lower, outer layer
13 Upper metal layer
14 Lower metal layer

The invention claimed is:

1. Package (1) for single-dose films (2) containing active substance, comprising an upper packaging material element (3) and a lower packaging material element (4) which are connected together by a peripheral seal area or respectively sealing seam (5) such that a cavity (6) for holding the film (2) is formed, said cavity being enclosed on all sides, wherein the upper packaging material element (3) and the lower packaging material element (4) each have at least one cut (7, 8) in the region of the seal area or respectively sealing seam (5), said cuts being congruent, and at least one cut (7, 8) is crossed by a folding or bending line (10), characterized in that the upper packaging material element (3) includes an upper outer layer (11) and an upper inner metal layer (13) and the lower packaging element (4) includes a lower outer layer (12) and a lower inner metal layer (14) and at least one of the upper packaging material element (3) and the lower packaging material element (4) includes a sealing layer (9) positioned between upper inner metal layer (13) and the lower inner metal layer (14), the folding or bending line (10) is formed in a weakened manner only in at least one of the upper outer layer (11) and the lower outer layer (12).

2. Package (1) according to claim 1,
characterized
in that the folding or bending line (10) is produced by perforation, notch punching, scoring or by laser ablation.

3. Package (1) according to claim 1,
characterized
in that the folding or bending line (10) is an interrupted line.

4. Package (1) according to claim 1,
characterized
in that the seal area or respectively the sealing seam (5) is not peelable.

\* \* \* \* \*